United States Patent [19]

Berg et al.

[11] Patent Number: 4,734,529
[45] Date of Patent: Mar. 29, 1988

[54] METHOD FOR THE ISOMERIZATION OF OXIRANES

[75] Inventors: Marion Berg, Rodenbach; Andreas Grund, Darmstadt; Guenter Prescher, Hanau, all of Fed. Rep. of Germany

[73] Assignee: Degussa Aktiengesellschaft, Frankfurt am Main, Fed. Rep. of Germany

[21] Appl. No.: 944,071

[22] Filed: Dec. 22, 1986

[30] Foreign Application Priority Data

Jan. 18, 1986 [DE] Fed. Rep. of Germany ....... 3601380

[51] Int. Cl.$^4$ ............................................. C07C 45/51
[52] U.S. Cl. .................................. 568/310; 568/341; 568/384
[58] Field of Search ........................ 568/310, 341, 384

[56] References Cited

U.S. PATENT DOCUMENTS

| | | | |
|---|---|---|---|
| 3,118,947 | 1/1964 | Amir | 568/384 |
| 3,151,167 | 9/1964 | Eisinmann et al. | 568/384 |
| 3,255,258 | 6/1966 | Charles et al. | 568/384 |
| 3,321,515 | 5/1967 | Moore et al. | 568/384 |
| 3,350,457 | 10/1967 | Price et al. | 568/341 |
| 3,542,883 | 11/1970 | Nenitescu et al. | 568/384 |
| 3,855,303 | 12/1974 | Bishop | 568/384 |
| 4,451,672 | 5/1984 | Gray | 568/384 |

FOREIGN PATENT DOCUMENTS 3136886  5/1983  Fed. Rep. of Germany ...... 568/341

Primary Examiner—James H. Reamer
Attorney, Agent, or Firm—Beveridge, DeGrandi & Weilacher

[57] ABSTRACT

The method for the isomerization of oxiranes of the general formula:

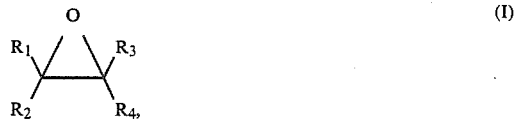

wherein $R_1$ and $R_3$ are hydrogen; $R_2$ is alkyl or alkylene groups of 3 to 26 carbon atoms or the phenyl group which may also be substituted, and $R_4$ is hydrogen or alkyl from 1 to 26 carbon atoms and in which the carbon atoms of the epoxy ring can also form components of a cyclic system, wherein as a catalyst there is used alkali iodide and a polyethyleneglycol with an average mol mass of 400 to 10,000 with a boiling point, preferably above the boiling point of the carbonyl compounds that are formed.

10 Claims, No Drawings

METHOD FOR THE ISOMERIZATION OF OXIRANES

The present invention relates to a method for the preparation of carbonyl compounds, which can be substituted, through the rearrangement of epoxy compounds.

The carbonyl compounds which are obtained as a result of the isomerization of epoxides are valuable intermediate products for organic synthesis and are useful raw materials for the chemical industry; for example, for cosmetics, pharmaceutical and for agrochemicals.

Because of these reasons, the isomerization reaction was frequently investigated, for example, with acidic or alkaline functioning catalyst systems, such as for example, borontrifluoride or tertiary potassiumbutylate.

With acidic catalysts, there is formed mixtures of ketones and aldehydes, whereas with alkaline or basic catalyst systems, primarily unsaturated alcohols are obtained.

The synthesis of the mixture of aldehydes and ketones fluctuated widely. So for example, epoxy fatty acid esters could be converted into ketofattyesters in the presence of borotrifluoride etherate in the presence of boiling dioxane for a yield of 70 to 90%. See J. Am. Oil Chem. Soc. 42 (1965), p. 126 ff. However this method was extremely problematical for a large scale production because of the easily inflammable dioxanes which were required to be introduced into the system in large amounts. Additionally, the borotrifluoride etherate has the disadvantage that it is highly corrosive and requires completely water-free solvents and starting materials.

In accordance with a more recent development, isomerizations of oxiranes have been carried out with acidic catalysts; namely, with hydrogen halides or their conversion products, in an aqueous medium which result in somewhat higher yields of the ketone compounds in the mixture; i.e. over 50%, particularly when the product distillation is carried out under an inert gas to remove the water.

Without the utilization of an inert gas, the yields obtained of the aldehyde-ketone mixture are less than 50%; see German OLS No. 33 34 600. Also, in the method shown in U.S. Pat. No. 4,451,672, the utilization of dicobaltcarbonyl in tertiary butylalcohol under an argon atmosphere is necessary.

Further, the methods which utilize inorganic metal salts such as shown in Japanese applications Nos. 72/40779 and 81/047442 are accompanied by severe difficulties when attempts are made to carry them out on a commercial scale. The separation of the catalyst which is obtained in the reaction mixture has been found to be very costly.

Methods which were not technically feasible because of the dangerous and harzardous nature of the starting materials are those which utilize lithiumbromide or perchlorate in the presence of phosphinoxide or phosphoric acid trisamide in benzene See J. Am. Chem. Soc. 93 (1971), p. 1963.

It is also known to use sodium iodide together with propyliodide. In that method, the solvent dimethylsulfoxide is utilized. See J. Chem. Soc. Chem. Comm. (1968), p. 227 ff. The catalyst mixture, however, must be utilized in a five fold excess. It resulted therefrom that the isolation of the product from the reaction mixture was very difficult because of the precipitated iodine. Therefore, the catalyst mixture that was introduced was only suitable for a single conversion because it was required to be washed with water.

In comparison, the method of preparation shown in DE-OS No. 31 36 886 leads to a ketone content in the aldehyde-ketone mixture of at least 75% with the utilization of sodium iodine alone in the presence of dimethylsulfoxide or dimethylformamide. The yields of ketone also are over 70%. The introduced catalyst can be utilized a plurality of times without a costly purification step. The ketone that is obtained as a result of the reaction must however be extracted from the dimethylsulfoxide or dimethylformamide through an aqueous extraction. The solvent materials that were introduced into this system were therefore lost.

It is therefore an object of the present invention to provide a technically feasible method for the preparation of carbonyl compounds in particular ketones, through the isomerization of corresponding epoxy compounds wherein the yield of the reaction mixture and in particular the content of ketone is at least equal to and preferably much higher than the known methods and to carry out this synthesis in a considerably simplified manner.

It has now been found in accordance with the present invention that this object can be accomplished when oxiranes represented by the general structural formula:

in which $R_1$ and $R_3$ are hydrogen;

$R_2$ is alkyl or alkylene of 3 to 26 carbon atoms or the phenyl group, which can also be substituted, $R_4$ is hydrogen or alkyl from 1 to 26 carbon atoms and in which the carbon atoms of the epoxy ring structure can optionally be components of a cyclic system, are converted to carbonyl compounds, especially ketones through the use of a catalyst system of an alkaliiodide and a polyethyleneglycol of the formula:

$$HO-(CH_2-CH_2-O)_nH, \qquad (II)$$

wherein n is the number of recurring units of $CH_2-CH_2-O$ such that the glycol has an average mol mass of 400–10,000.

The isomerization is carried out at a temperature of 120° to 250° C., preferably 170°–200° C. The above-mentioned oxiranes are known compounds.

Among the epoxy alkanes, the α- or 1,2-epoxyalkanes are particularly suitable for purposes of the invention and include as representative examples epoxydecane, epoxydodecane, epoxytetradecane, epoxyhexadecane and 1,2-epoxy-3,3-dimethylbutane.

Oxiranes that have been found particularly good insofar as both of their carbon atoms of the epoxy ring are components of the cyclic system are, for example, oxiranes of cyclic olefins such as cyclohexeneoxide, cyclohepteneoxide, cycloocteneoxide, 1,2-epoxycyclododecanediene-5,9; and cyclododecenoxide.

In addition to individual groups, mixtures can also be utilized.

By phenyl groups substituted oxiranes such as styrene oxide, or 1-(1,2-epoxy-propyl)-3,4-methylenedioxybenzene can also be used.

As the alkali iodide, there can be mentioned sodium and potassium iodide, preferably sodium iodide.

The polyethyleneglycols utilized for purposes of the invention are preferably those of an average mol mass of 400–1,000 and in particular, those which have an average molecular weight of about 400.

The catalyst system of alkali iodide and polyethyleneglycol contains 0.1 to 10 weight percent of potassium iodide and 5–50 weight percent polyethyleneglycol, based on the amount of oxirane in the system.

Preferably, catalyst systems which contain 1 to 5 weight percent sodium iodide and 15 to 30 weight percent of polyethyleneglycol, based on the amount of oxirane introduced are preferred. Larger amounts of polyethyleneglycol and sodium iodide are not critical; with smaller amounts, the reaction velocity falls.

As particularly suitable for the carrying out of the method of the present invention are those polyethyleneglycols which have a boiling point above that of the carbonyl compounds produced in the reaction, and in particular above that of the ketones produced. In this manner, it is possible to distillatively remove from the reaction mixture the more easily boiling carbonyl compounds. The catalyst system of sodium iodide and polyethyleneglycol remains as a residue which can be immediately used again for its intended purpose without any purification or any other treatment.

The method of the present invention is a considerable step forward in the art as compared to the known level of technology in which the catalyst was either lost or only could be further used as a catalyst after considerable treatment.

In addition, there was frequently obtained an aqueous waste such as, for example, heavy metal salts which entail expensive and cumbersome methods for removal; see Japanese applications Nos. 72/40779 and 81/047442.

It could not be expected that the epoxide could be converted at temperatures above 100° C. in the presence of hydroxy group containing components and that there would be obtained ring opening products through hydroxyl groups only in very low amounts. Moreover, in the isomerization of oxiranes surprisingly no product mixture was obtained in accordance with the reaction:

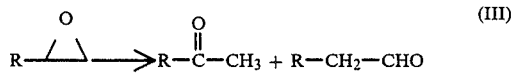

(III)

That is, methylketone and aldehyde were not obtained. Instead, there was obtained almost exclusively the methylketone product. The yields of this methylketone product as a rule was at least 80 to 90%. The method of the present invention was characterized in that particularly good results are obtained in the production of pinacolone from 1,2-epoxy-3,3-dimethylbutane.

In the method described in U.S. Pat. No. 4,517,386, oxiranes are converted with lithiumtetrafluorborate in the presence of polyethers, that is, with components having no hydroxy groups, and mixtures are obtained which almost exclude any aldehyde content. Therefore, the present invention was fully unexpected from the prior art because in accordance with the procedures of the present invention only very significant yields were obtained.

With the utilization of cyclic alkenoxide, there is developed in high yield the cycloalkanones in accordance with the following general reaction equation:

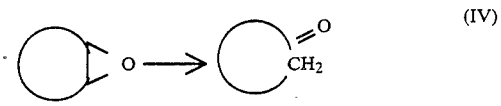

(IV)

The yields generally range over 80%. Ring contracting products such as are described as principle products by K. Arata, Catal. Rev. Sci. Eng. 25 (3), p. 365 (1983) are obtained, if at all, only in negligible amounts.

In addition to α-oxiranes and cyclic oxiranes, linear oxiranes with interior epoxy groups can also be used.

The preparation of the epoxides that are used as starting materials can be obtained from mono-olefine fractions which contain compounds with different chain lengths. The above-mentioned formula (I) corresponds to mixtures of epoxy compounds with 8 to 28 carbon atoms.

In oxiranes with interior epoxy groups, the epoxy groups can be arbitrarily distributed along the carbon atom chain, and can be included in the oxirane mixture.

In accordance with the carrying out of the method of the present invention, the starting materials are brought into contact with the polyethyleneglycol and the alkali iodide and are stirred together at the abovementioned temperatures for longer periods of time, as for example 2 to 10 hours. The course of the reaction can be easily determined by known methods such as for example, through gas chromatography.

The utilization of an inert gas is not necessary.

The method of the present invention can be carried out under different pressures such as, for example, under normal pressure; the method can also be carried out utilizing excess pressure or reduced pressure. It is only essential that the reaction temperature be reached during the course of the reaction.

The conversion reaction can also be carried out in a discontinuous as well as a continuous method in any suitable reaction vessel as will be apparent to those skilled in the art. For example, there can be used stirred vessels, cascades of vessels, tube or circulatory reactors wherein the heat of the reaction can be attained through any suitable means and can be also removed by any conventional means. Suitable materials for these reaction apparatus are, for example, glass, stainless steel as well as enameled material.

The technical advantage of the present invention as has already been mentioned above resides in the great facility with which the method can be carried out, and the convenience with which the reaction mixture after completion of the reaction can be distillatively separated into its component parts at the head of the reaction vessel to obtain the reaction product which is removed, and the residue, which is the remaining catalyst system.

In spite of the simplicity of the isomerization reaction of the present invention, the yield of the carbonyl compounds is not only at least as high as with the known methods but almost always is considerably higher.

With the introduction of α-oxiranes, there is obtained for the first time a reaction mixture which consists almost completely of the methylketone that is concerned herein. The catalyst system which remains or sinks to the sump in the reaction vessel can immediately be utilized for further preparation of carbonyl compounds and any subsequent purification methods for the separation and removal of the catalyst are unnecessary.

Particularly advantageous is the utilization of polyethyleneglycols because these are completely non-toxic as well as physiologically harmless. Because of their very high flammability point and their trouble-free biological degradation, they are particularly suitable for purposes of the present invention in the utilization of the conversion reaction.

The following examples illustrate the more detailed aspects of the present invention. In carrying out the examples, the following procedures were utilized:

The epoxy compound in the amount of 100 g as identified in Table 1 is mixed with the given amount of polyethyleneglycol as set forth in Table 1 with a molecular weight of 400, 600, 2,000, or 10,000 and sodium iodide, whereby the amounts in percent are based on the amount of epoxy introduced.

The mixture is then thoroughly stirred and heated to the given temperature, and a reflux can be utilized at the same time.

The conversion of the epoxide is determined and followed by gas chromatographic methods. After the completion of the reaction, the product is distilled, optionally under vacuum, and is separated from the reaction mixture. A small amount of low boiling components can be separated therefrom as a preliminary step.

The residue from the distillation is immediately suitable for the following conversion reaction as a catalyst.

In Example 14, instead of polyethyleneglycol there is used diglyme; that is, diethyleneglycol dimethylether.

All percentage amounts are in weight percent.

EXAMPLE 15

Into a 100 l stainless steel still there is introduced 26.5 kg cycloocteneoxide and 8.0 kg polyethyleneglycol (average M=400) and 1.5 kg sodium iodide which is heated for 10 hours at 185° C. The conversion of epoxide was 99.8%. The product is then cooled to 100° C. and then is treated by distillation under vacuum. After a small amount of initial runnings, (1.75 kg; 57% product) there was obtained at 96° C. and 15 mm, 21 kg ketone in a purity of 99%. The yield was 86%.

Further variations and modifications of the foregoing invention will become apparent to those skilled in the art and are intended to be encompassed by the claims appended hereto.

The German application No. P 36 01 380.3 is relied on and incorporated herein.

We claim:

1. A method for the isomerization of an oxirane selected from the group consisting of:
   α epoxyalkane having 10 to 16 carbon atoms,
   1,2-epoxy-3,3-dimethylbutane,
   cycloalkenoxide with 6 to 12 carbon atoms,
   1,2-epoxycyclododecandiene-5,9,
   styrene oxide,
   1-(1,2-epoxypropyl)-3,4-methylenedioxybenzene,
   1,2,7,8-diepoxyoctane, and
   neohexenoxide,
   comprising contacting said oxirane at an elevated temperature to a catalyst system composed of an alkali iodide and the polyetyleneglycol represented by the formula:

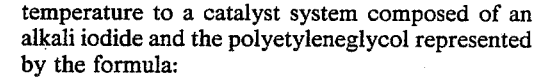

wherein n is the number of recurring units of $CH_2$—$CH_2$—O such that said glycol has an average

TABLE 1

| No. | Epoxide | Product | PEG | % PEG | % NaI | T (°C.) | Reaction Time | Conversion Epoxide | Yield | Remarks |
|---|---|---|---|---|---|---|---|---|---|---|
| 1 | 1,2-epoxydecane | 2-decanone | PEG 400 | 30 | 6 | 185 | 5.5 | 97.3 | 94.8 | |
| 2 | 1,2-epoxydodecane | 2-dodecanone | PEG 400 | 30 | 6 | 191 | 3 | 99.0 | 88.7 | |
| 3 | 1,2-epoxytetradecane | 2-tetradecanone | PEG 2000 | 25 | 6 | 193 | 5 | 98.6 | 90.1 | |
| 4 | 1,2-epoxyhexadecane | 2-hexadecanone | PEG 10000 | 25 | 5 | 180 | 5.5 | 92.5 | 86.7 | |
| 5 | 1,2,7,8-diepoxyoctane | 2,7-octandione | PEG 400 | 30 | 6 | 155 | 7 | 99.3 | 73.1 | |
| 6 | styroloxide | acetophenone | PEG 600 | 20 | 4 | 144 | 4 | 62.5 | 52.4 | |
| 7 | Cycloheptenoxide | cycloheptanone | PEG 400 | 30 | 6 | 183 | 7 | 97.4 | 92.8 | |
| 8 | cyclooctenoxide | cyclooctanone | PEG 400 | 30 | 5 | 190 | 8 | 99.6 | 85.2 | |
| 9 | cyclooctenoxide | cyclooctanone | PEG 400 | Dest.-Res. of Ex. 8 | | 190 | 4.5 | 99.8 | 99.7 | |
| 10 | cyclooctenoxide | cyclooctanone | PEG 400 | Dest.-Res. of Ex. 9 | | 191 | 4.5 | 99.7 | 87.0 | |
| 11 | 1,2-epoxycyclododecadiene-5,9 | cyclododecadiene-3,7-on-1 | PEG 400 | 40 | 3 | 195 | 9 | 99.5 | 98.7 | |
| 12 | Neohexenoxide | Pinakotone | PEG 400 | 30 | 6 | 180 | 6 | 99.6 | 85.6 | in autoclaves |
| 13 | 1-(1,2-epoxypropyl)-3,4-methylenedioxybenzene | 3,4-methylenedioxybenzylmethymethylketone | PEG 2000 | 31 | 5 | 180 | 8 | 99.2 | 46.0 | |
| 14 | cyclooctenoxide | cyclooctanone | Diglyme | 30 | 6 | 182 | 6 | 9.6 | 9.4 | a comparative example |

In the table, "PEG" means polyethyleneglycol. With Example 9, the distillation residue of Example 8 was introduced as catalyst. In the same manner, the residue of Example 9 was introduced as catalyst in Example 10.

$$HO_M\text{—}(CH_{2M}\text{—}CH_{2M}\text{—}O)_{nM}H \qquad (II)$$

mol mass of 400 to 10,000, at a temperature of 120° to 250° C.

2. The method in accordance with claim 1 wherein the polyethyleneglycol has an average mol mass of 400 to 1,000.

3. The method of claim 1 wherein the polyethyleneglycol has an average mol mass of about 400.

4. The method according to claim 1 wherein the alkali iodide is sodium iodide.

5. The method in accordance with claim 1 wherein the catalyst system contains 5 to 50 weight percent polyethyleneglycol and 0.5 to 10 weight percent alkali iodide.

6. The method in accordance with claim 5 wherein the alkali iodide is sodium iodide.

7. The method in accordance with claim 5 wherein the catalyst system contains 15-30 weight percent polyethyleneglycol and 1.5 weight percent alkali iodide based on the weight of the oxirane.

8. The method in accordance with claim 7 wherein the alkali iodide is sodium iodide.

9. The method in accordance with claim 1 wherein the polyethyleneglycol has a boiling point above the boiling point of the reaction mixture.

10. The method in accordance with claim 1 wherein the polyethyleneglycol has a boiling point above the boiling point of the ketone obtained in the reaction mixture.

* * * * *